US010196340B2

United States Patent
Wang et al.

(10) Patent No.: US 10,196,340 B2
(45) Date of Patent: Feb. 5, 2019

(54) CLEAN PROCESS FOR PREPARING CHLOROFORMYL-SUBSTITUTED BENZENE (71) Applicant: Finings Co. Ltd., Huai'an, Jiangsu (CN)

(72) Inventors: Nongyue Wang, Shanghai (CN); Xiongwei Qu, Shanghai (CN); Guohua Li, Shanghai (CN); Jianming Shao, Shanghai (CN); Quanzhong Zhao, Shanghai (CN); Guoqiang Wen, Shanghai (CN)

(73) Assignee: Finings Co. Ltd., Huai'an, Jiangsu (CN)

( * ) Notice: Subject to any disclaimer, the term of this patent is extended or adjusted under 35 U.S.C. 154(b) by 0 days.

(21) Appl. No.: 15/629,617

(22) Filed: Jun. 21, 2017

(65) Prior Publication Data
US 2017/0283360 A1    Oct. 5, 2017

Related U.S. Application Data (63) Continuation of application No. PCT/CN2015/079272, filed on May 19, 2015.

(30) Foreign Application Priority Data

Dec. 22, 2014  (CN) .......................... 2014 1 0814971

(51) Int. Cl.
C07C 51/64     (2006.01)
C07C 63/70     (2006.01)
C07C 63/10     (2006.01)
C07C 63/30     (2006.01)
C07C 63/307    (2006.01)
C07C 63/34     (2006.01)

(52) U.S. Cl.
CPC .............. C07C 51/64 (2013.01); C07C 63/10 (2013.01); C07C 63/30 (2013.01); C07C 63/307 (2013.01); C07C 63/70 (2013.01); C07C 63/34 (2013.01)

(58) Field of Classification Search
CPC ....... C07C 63/10; C07C 63/30; C07C 63/307; C07C 63/70; C07C 51/64; C07C 63/34; C07C 17/06; C07C 25/10; C07C 45/43; C07C 45/455; C07C 47/55; B01J 2219/0871; C01B 7/04
See application file for complete search history.

(56) References Cited

U.S. PATENT DOCUMENTS

| 3,816,287 A | 6/1974 | Bockmann et al. |
| 4,056,455 A | 11/1977 | Lademann et al. |
| 4,165,337 A * | 8/1979 | Yoshinaka .............. C07C 17/14 204/157.99 |
| 4,276,231 A * | 6/1981 | Bockmann .............. C07C 51/58 423/240 R |
| 5,514,254 A | 5/1996 | Ribaldo |
| 9,556,090 B2 | 1/2017 | Wang et al. |
| 2004/0052718 A1 | 3/2004 | Walsdorff et al. |
| 2007/0274901 A1* | 11/2007 | Wolf ..................... B01J 8/0453 423/502 |
| 2008/0159948 A1* | 7/2008 | Sesing ..................... C01B 7/04 423/502 |
| 2011/0278174 A1 | 11/2011 | Ooms et al. |

FOREIGN PATENT DOCUMENTS

| CN | 1948245 A | 4/2007 |
| CN | 102344362 A | 2/2012 |
| CN | 102502498 * | 6/2012 |
| CN | 102502498 A | 6/2012 |
| CN | 102516060 A | 6/2012 |
| DE | 3146868 A1 | 7/1982 |
| JP | 51-008223 A | 1/1976 |
| JP | 57-130931 A | 8/1982 |
| JP | 61-218536 A | 9/1986 |

OTHER PUBLICATIONS

Studt et a. (Volcano Relation for the Deacon Process over Transition-Metal Oxides, ChemCatChem, 2, pp. 98-102, published 2010) and '948 (US PGPub, 2008/0159948, Published 2008) (Year: 2008).*
CN102502498 translated (Year: 2014).*
U.S. Appl. No. 15/629,569, Shanghai Fanglun New Material Technology Co., Ltd., Jun. 21, 2017.
Norman Rabjohn et al., "The chloromethylation of toluene and conversion of p-xylyl chloride to terephthaloyl chloride," Journal of the American Chemical Society, vol. 76, No. 21, pp. 5479-5481 (Nov. 1, 1954).
Javier Perez-Ramirez et al., "Sustainable chlorine recycling via catalysed HCl oxidation: from fundamentals to implementation," Energy & Environmental Science, vol. 4, No. 12, pp. 4786-4799 (Sep. 30, 2011).

* cited by examiner

Primary Examiner — Yevgeny Valenrod
Assistant Examiner — Blaine G Doletski
(74) Attorney, Agent, or Firm — Mei & Mark LLP; Manni Li (57) ABSTRACT Clean process for preparing a chloroformyl-substituted benzene by oxidation of a tail gas hydrogen chloride from a chlorination reaction and a chloroacylation reaction and recycling of the resulting oxidation product chlorine gas into the chlorination reaction. The present invention provides a clean process for preparing a polymer-grade chloroformyl-substituted benzene.

21 Claims, 1 Drawing Sheet

CLEAN PROCESS FOR PREPARING CHLOROFORMYL-SUBSTITUTED BENZENE

CROSS-REFERENCE TO RELATED APPLICATIONS

The subject application is a continuation of PCT/CN2015/079272 filed on May 19, 2015 and claims priority on Chinese application no. 201410814971.X filed on Dec. 22, 2014. The contents and subject matter of the PCT and Chinese priority application are incorporated herein by reference.

TECHNICAL FIELD

The present invention relates to a method for preparing chloroformyl-substituted benzene, particularly, a clean method for preparing chloroformyl-substituted benzene through oxidation of a tail gas hydrogen chloride.

BACKGROUND OF THE INVENTION

Known methods for preparing chloroformyl-substituted benzenes mainly include the photochlorination method (see DE3146868 and JP57-130931), sulfoxide chloride method, phosphorus trichloride method, phosphorus pentachloride method, and phosgene method. The sulfoxide chloride method is the most commonly used (see, for example, CN102516060A and CN102344362A). However, the method requires the use of phthalic acid having a high purity of 99.99% as a raw material, which results in high cost. Moreover, these methods all suffer from a problem of generation of environmentally unfriendly by-products such as hydrogen chloride, sulfur dioxide, carbon dioxide, and phosphorous acid. These by-products cause inconvenience to subsequent treatments of products and likely lead to environmental pollution.

The photochlorination method may use methyl aromatic compounds as raw materials, but the amount of the by-product hydrogen chloride is enormous. How to deal with the large amount of hydrogen chloride has become an issue to be urgently solved. Currently, the main measure actually adopted in the industry is to absorb hydrogen chloride with water to prepare low-value and inexpensive hydrochloric acid for sale; since hydrochloric acid is inexpensive and has limited market demand, the preparation of hydrochloric acid from hydrogen chloride has become a burden rather than a resource. Another measure is to neutralize hydrogen chloride with a base for direct discharge; however, with increasing sophistication of environmental laws and regulations, environmental protection standards of various ways of discharge have become very stringent.

The method for preparing chlorine gas directly from the by-product hydrogen chloride can not only achieve closed circulation of chlorine element, but also achieve zero emissions in the reaction process, which greatly improves the level of energy saving and emission reduction in the industry, reduces the cost, and eliminates pollution to the environment. Up to now, the methods of preparing chlorine gas from hydrogen chloride can be divided into three main categories: electrolytic method, direct oxidation method, and catalytic oxidation method. The electrolytic process has a high energy consumption and uses an ionic membrane that needs to be frequently replaced, resulting in a very high cost, wherein the cost per ton chlorine gas recovered is greater than 4,000 RMB Yuan. The direct oxidation method suffers from a low yield and cannot be industrialized. In contrast to the electrolytic method and the direct oxidation method, the catalytic oxidation method, particularly the Deacon catalytic oxidation, exhibits the highest potential for industrialization.

Chlorine gas used in many productions in the chlorination industry is required to be ≥99.6% (vol %). Therefore, for chlorine gas obtained from the Deacon reaction, a high-purity chlorine gas capable of being recycled can be obtained only after a problem of separation of the resulting mixed gas from the reaction is solved. Particularly, to recover chlorine gas from a mixed gas from oxidation of hydrogen chloride, a separation method of hydrogen chloride by absorption with water is generally adopted, for examples, CN102502498A and US2008/0159948A1, which generates a large amount of dilute hydrochloric acid and thus require further treatments.

In view of the above, there is a need in the art for a clean process for producing chloroformyl-substituted benzenes with low cost, good quality, and no pollution that is capable of achieving closed circulation of chlorine resources. The key of the clean process lies in the oxidation process of hydrogen chloride and separation process of the product gas stream. Once the critical processes are solved, a high-purity chlorine gas may be obtained, thus achieving recycle of chlorine gas. The clean production process of chloroformyl-substituted benzenes is the key to achieve industrialization of related chemical industries, for example, the aramid industry.

SUMMARY OF THE INVENTION

The process of the present invention is achieved by oxidizing a tail gas hydrogen chloride from a chlorination reaction and a chloroacylation reaction and recycling of the resulting oxidation product chlorine gas into the chlorination reaction. The present invention provides a clean process of preparing a polymer-grade chloroformyl-substituted benzene.

The present invention provides a clean process of preparing a chloroformyl-substituted benzene. The process of the present invention solves the existing problems in the art, achieves closed circulation of chlorine resources, fundamentally eliminates pollution caused by by-products, and provides a product with low cost and high quality.

The present invention is achieved by the following technical solution: firstly, reacting a methyl aromatic hydrocarbon of formula $(X)_a C_6 H_{6-a-b}(CH_3)_b$ or a pendant alkyl chloride thereof with chlorine gas (e.g. under illumination conditions) to prepare trichloromethyl-substituted benzene; further reacting the resulting trichloromethyl-substituted benzene to prepare chloroformyl-substituted benzene; subjecting the resulting HCl gas to catalytic oxidation according to the Deacon reaction to generate chlorine gas for further use in the chlorination of the methyl aromatic hydrocarbon to prepare the trichloromethyl-substituted benzene. Representative equations of the overall technical process are as follows:

For simplicity, only the methyl aromatic hydrocarbon is shown in the equations. Those skilled in the art understand that the pendant alkyl chloride of the methyl aromatic hydrocarbon is subjected to similar reactions.

The chlorine gas obtained by the oxidation is introduced into the chlorination reaction again as a raw material. Altogether, the complete equation for preparing the bis-(chloroformyl)-benzene of the present invention is:

Those skilled in the art understands that the reactions for preparing the acyl chloride using water and the trichloromethyl-substituted benzene also have similar complete equation.

$(X)_aC_6H_{6-a-b}(CH_3)_b$ is a methyl aromatic compound (a pendant alkyl chloride thereof also applies to the present invention), $(X)_aC_6H_{6-a-b}(CCl_3)_b$ is trichloromethyl-substituted benzene, where $(X)_aC_6H_{6-a-b}(COOH)_b$ is a corresponding aromatic acid, and $(X)_aC_6H_{6-a-b}(COCl)_b$ is chloroformyl-substituted benzene. In the formulae of the compounds of the present application, X is a chlorine, bromine or fluorine atom, a is an integer selected from 0, 1, 2, 3, 4 and 5, b is an integer selected from 1, 2, 3 and 4, and a+b≤6.

The term "corresponding aromatic acid" in the present application means that a substituent on a parent nucleus of the aromatic acid and a substituent on a parent nucleus of the methyl aromatic hydrocarbon are located at the same substitution position or corresponding substitution positions; the substituent on the parent nucleus of the aromatic acid and the substituent on the parent nucleus of the methyl aromatic hydrocarbon may also be the same.

The term "pendant alkyl chloride of the methyl aromatic compound" in the present application means a compound where hydrogen atoms of a alkyl group in the aromatic compound are not completely substituted by chlorine atoms; the target product of the photochlorination reaction in the present application, i.e., trichloromethyl-substituted benzene, means a product where hydrogen atoms of a alkyl group in the aromatic compound are completely substituted by chlorine atoms.

A clean process for preparing the chloroformyl-substituted benzene of the present invention comprises the following steps:

Step 1 (chlorination reaction): reacting a methyl aromatic hydrocarbon of formula $(X)_aC_6H_{6-a-b}(CH_3)_b$ or a pendant alkyl chloride thereof with chlorine gas (e.g. under illumination conditions) to prepare a trichloromethyl-substituted benzene and obtain a by-product hydrogen chloride;

Step 2 (chloroacylation reaction): further reacting the resulting trichloromethyl-substituted benzene in step 1 with the corresponding aromatic acid of formula $(X)_aC_6H_{6-a-b}(COOH)_b$ or water to prepare the chloroformyl-substituted benzene and to obtain a by-product hydrogen chloride;

Step 3 (catalytic oxidation of the by-product hydrogen chloride): subjecting the collected by-product hydrogen chloride in steps 1 and 2 to catalytic oxidation in the presence of a catalyst (the Deacon reaction) to prepare chlorine gas;

Step 4 (separation of the gas stream from step 3): separating a product gas stream from step 3 to obtain gas streams containing chlorine, containing oxygen, and/or containing hydrogen chloride;

Step 5 (recycling of the separated substances): introducing the gas stream containing chlorine separated in step 4 as a raw material into the chlorination reaction including step 1; and Optionally, introducing the gas streams containing hydrogen chloride and/or containing oxygen separated in step 4 as a raw material into the catalytic oxidation of the by-product hydrogen chloride in step 3.

In the clean process for preparing the chloroformyl-substituted benzene of the present invention, a purification step of the trichloromethyl-substituted benzene may be further used after the chlorination reaction; and a purification step of chloroformyl-substituted benzene may further be used after the chloroacylation reaction.

The process of the present invention is a completely green chemical process, without any wastes except for normal losses during the purification and reaction. The process of the present invention achieves a clean production of chloroformyl-substituted benzene, particularly a raw material for preparing aramid, polymer-grade bis-(chloroformyl)-benzene, and thus has important economic value and social benefit for producing high-performance aramid fibers at low cost.

The present invention has the following advantageous effects.

1) In the present invention, the by-product hydrogen chloride generated in the chlorination and chloroacylation steps during the process of producing chloroformyl-substituted benzene, for example, bis-(chloroformyl)-benzene, is further subjected to catalytic oxidation to prepare chlorine gas, and the obtained chlorine gas is recycled to the chlorination reaction, thereby achieving closed circulation of chlorine element, and thus reducing the production cost and reducing the environmental pollution.

2) The catalytic oxidation in step 3 of the present invention is the key and core to achieve recycling of chlorine resources, and in the step, the resulting product gas stream in the catalytic oxidation of hydrogen chloride is directly circulated without separation thereof, achieving the dissipation effect of heat during the Deacon reaction and prolonging the lifetime of catalysts, and also the use of heat carried by the circulated product gas stream itself reduces the fuel cost in preheating a feed gas containing hydrogen chloride, further saving the industrialization cost.

3) In step 4, the present invention adopts a separation method comprising condensation, drying, and adsorption steps to separate the product gas stream of step 3, and the separation method optionally further comprises a liquefaction step. The separation method of the present invention does not produce a large amount of dilute hydrochloric acid because a water washing step is not present. Particularly, when the hydrogen chloride concentration in the chlorine gas after oxygen gas is removed by condensation, drying, and adsorption is low, a further liquefaction step is not required. Because the chlorine gas containing a small amount of hydrogen chloride gas is directly recycled to a chlorination step, for example, step 1, the presence of the small amount of hydrogen chloride does not affect the reaction between the chloride gas and the methyl aromatic hydrocarbon to produce the trichloromethyl-substituted benzene.

The separation method of the product gas stream in step 4 of the present invention has the advantages of simple process flow, environmental friendliness, low energy consumption, high separation efficiency, and low cost, and the purity of chlorine gas in the gas stream containing chlorine recovered by the separation method is up to ≥99.6% (vol %), which can meet the quality requirements of chlorine feed gas in the photochlorination reaction.

4) In the process of the present invention, in addition to closed circulation of chlorine resources, other substances generated during the production of the product may also be recycled, thereby achieving a clean production. For example, hydrogen chloride and/or oxygen gas that is not completely reacted in the catalytic oxidation in step 3 can be subjected to the catalytic oxidation again after being separated.

5) According to the process of the present invention, the polymer-grade chloroformyl-substituted benzene, for example, bis-(chloroformyl)-benzene, can be obtained, and the production cost is lower than that of the conventional process by above 30%.

DETAILED DESCRIPTION OF THE INVENTION

Figure 1:
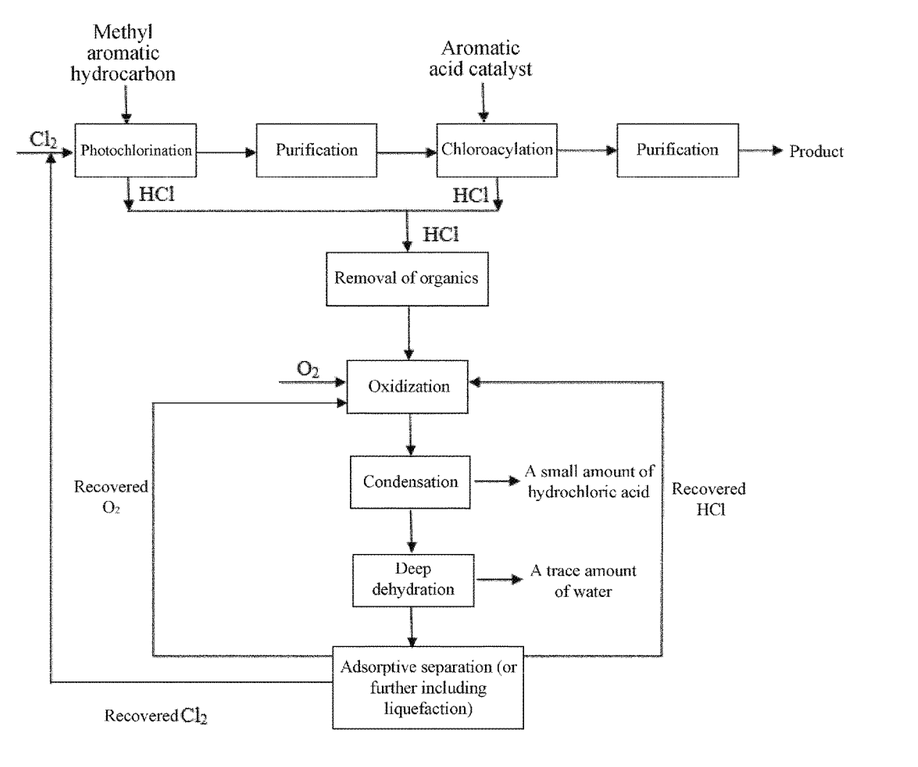
The FIGURE is a flow diagram showing the process for preparing bis-(chloroformyl)-benzene of the present invention.

The methods for preparing chloroformyl-substituted benzene in the existing technology all suffer from the problems of a lot of by-products, difficulties in handling, low product yield, and serious environmental pollution, etc. To obtain a high quality of chloroformyl-substituted benzene, enormous economic and environmental costs are required. After extensive research and experimentation, the present inventors creatively combine chlorination of the methyl aromatic hydrocarbon, synthesis of chloroformyl-substituted benzene, and oxidation of hydrogen chloride to prepare chlorine gas into a complete process (also with the improvement of the oxidation process of hydrogen chloride and the separation process of the mixed gas), wherein a large amount of hydrogen chloride generated during the chlorination and the chloroacylation is subjected to the catalytic oxidation to prepare chlorine gas and the resulting chlorine gas is introduced into the chlorination process again, achieving recycling of chlorine element.

The whole process is a clean production process, which is carried out in the following steps:

Step 1 (chlorination reaction): reacting a methyl aromatic hydrocarbon of formula $(X)_a C_6 H_{6-a-b} (CH_3)_b$ or a pendant alkyl chloride thereof with chlorine gas (e.g. under illumination conditions) to prepare a trichloromethyl-substituted benzene and obtain a by-product hydrogen chloride, where X is a chlorine, bromine or fluorine atom, a is an integer selected from 0, 1, 2, 3, 4 and 5, b is an integer selected from 1, 2, 3 and 4, and a+b≤6.

The term "pendant alkyl chloride of the methyl aromatic compound" in the present application means a compound where hydrogen atoms of a alkyl group in the aromatic compound are not completely substituted by chlorine atoms; the target product of the photochlorination reaction in the present application, i.e. trichloromethyl-substituted benzene, means a product where hydrogen atoms of a alkyl group in the aromatic compound are completely substituted by chlorine atoms.

During the chlorination reaction of the present invention, the resulting trichloromethyl-substituted benzene is optionally subjected to further purification or directly fed to the chloroacylation reaction, and the resulting by-product hydrogen chloride is recovered for use in step 3.

The chlorination reaction of the present invention relates to a photochemical method for preparing trichloromethyl-substituted benzene, characterized in that a methyl aromatic hydrocarbon of formula $(X)_a C_6 H_{6-a-b} (CH_3)_b$ or a pendant alkyl chloride thereof is reacted with chlorine gas under illumination conditions to prepare trichloromethyl-substituted benzene, where the illumination has a light source wavelength of about 350 nm-700 nm and a light amplitude of no more than about 200 nm, and where chlorine gas feeding is initiated under conditions of a reaction temperature of about 0° C.-85° C. and an illuminance of about 2000 Lux-about 55000 Lux, for a first reaction stage where the reaction temperature is no more than about 120° C. at the illuminance; and then the remaining amount of chlorine gas is fed at a higher reaction temperature until the reaction is completed. In a preferred aspect of the method, the light source preferably is an LED lamp.

The present inventors have found that, in the first reaction stage of chlorination, it is advantageous to consume preferably at least about ⅙ of a total amount of chlorine gas required by the reaction before increasing the temperature and illuminance. In some preferred aspects of the present invention, about ⅙-about ½ of the total amount of chlorine gas required by the reaction is consumed in the first reaction stage; and preferably, about ¼-about ⅓ of the total amount of chlorine gas required by the reaction is consumed in the first reaction stage.

The present inventors have found that, the reaction temperature in the first reaction stage of chlorination is preferably about 55-85° C.

The present inventors have found that, the illuminance in the first reaction stage of chlorination is about 5000 Lux-about 55000 Lux, preferably about 20000 Lux-about 55000 Lux, more preferably about 35000 Lux-about 45000 Lux.

The present inventors have found that, in the reaction after the first reaction stage of chlorination, the remaining amount of chlorine gas is fed at a reaction temperature of no more than about 350° C. and at an illuminance of no more than about 100000 Lux. The process following the first reaction stage of chlorination according to the method of the present invention may be a single reaction stage or divided into several reaction stages such as two, three, four, five, six, seven, eight, nine, or ten reaction stages. In the process following the first reaction stage, the illuminance is optionally increased when the temperature is increased in each stage. Preferably, the process following the first reaction stage in the photochlorination reaction may be further divided into second and third reaction stages. In the second reaction stage, the reaction temperature is controlled to be about 120° C.-about 160° C., the incoming illuminance is about 10000 Lux-about 70000 Lux, and ¼-⅔ of the total amount of chlorine gas is fed; and in the third reaction stage, the temperature is controlled to be about 160° C.-about 300° C., the incoming illuminance is about 50000 Lux-about 100000 Lux, and the remaining amount of chlorine gas is fed. In the second and third reaction stages, increasing the temperature and increasing the illuminance may be performed in any order.

The LED in the chlorination according to the method of the present invention preferably has a peak wavelength ranging from 350 nm-490 nm or 460 nm-490 nm. The light source in the chlorination according to the method of the present invention preferably has a light amplitude of no more than about 50 nm, preferably about 10 nm-about 30 nm, more preferably about 10 nm-about 25 nm.

In the reaction system of the chlorination reaction according to the method of the present invention, preferably, no solvent and initiator are added.

The expression "total amount of chlorine gas" in the chlorination of the present invention means the amount of chlorine gas required for complete chlorination of hydrogen atoms on side chains in the methyl aromatic hydrocarbon, which is at least a theoretical molar amount for chlorination of the raw material methyl aromatic compound. Taking xylene as an example, the total amount of chlorine gas is a molar amount that is at least six times the number of moles of the raw material xylene. Preferably, the total amount of chlorine gas in the chlorination of the present invention is a molar amount that is above six times the number of moles of xylene. The excess amount of chlorine gas may be conventionally determined. Preferably, for saving the reaction time, fed amounts of chlorine in the respective stages herein may be adjusted depending on the monitored reaction results.

The term "light amplitude" in the present invention means the wavelength range at half peak height of light emission by the light source, not the peak wavelength of light. For example, a light amplitude of 50 nm means that the wavelength range at half peak height of light emission by the light source is no more than 50 nm. The peak wavelength of the LED light source in the present invention may vary from 350 nm-700 nm, and for any given wavelength, the light source of incident light in the present invention enables the light amplitude to be controlled within 50 nm, for example peak amplitude 50 nm at 465 nm, peak amplitude 50 nm at 360 nm, peak amplitude 50 nm at 586 nm. The present inventors have found that the LED light source also has the advantage of less heat generation, and thus the cost of the production equipment can be reduced, for example no additional cooling device is needed. In contrast, for the photochlorination reaction using a high-pressure mercury lamp as a light source, a corresponding cooling device is required (for example, see U.S. Pat. No. 5,514,254).

The illuminance in the present invention may be determined by a conventional instrument such as illuminometer in the art. The wavelength in the present invention may be determined by a conventional instrument such as monochromator in the art.

The term "about" in the present invention means that with respect to temperature, positive or negative variation of a stated value is no more than 2.5° C. (expressed as the stated value ±2.5° C.), preferably the stated value ±2.5° C., ±2° C. or ±1° C.; means that with respect to illuminance, positive or negative variation of a stated value is no more than 2500 Lux (expressed as the stated value ±2500 Lux), preferably the stated value ±2500 Lux, ±2000 Lux, ±1500 Lux, ±1000 Lux, ±500 Lux, ±200 Lux or ±100 Lux; means that with respect to wavelength, positive or negative variation of a stated value is no more than 5 nm (expressed as the stated value ±5 nm), preferably the stated value ±4 nm, ±3 nm or ±1 nm; and means that with respect to light amplitude, positive or negative variation of a stated value is no more than 3 nm (expressed as the stated value ±3 nm), preferably the stated value ±2 nm or ±1 nm.

In the reaction system of the chlorination reaction according to the present invention, preferably, no solvent and initiator are added, and more preferably, no components other than xylene and chlorine are added. At various stages in the chlorination of the present invention, the reaction progression may be monitored by conventional sampling and detection methods such as gas chromatography, so as to suitably adjust the parameters described above, thereby saving the reaction time. The description about the durations for three stages is not limiting and the reaction time at each stage may be freely adjusted depending on the monitored results of chlorination progression. The speed of feeding chlorine gas herein is not limited to a particular feeding rate. When the expression such as slowly, gradually is used to describe the speed of feeding chlorine gas, its meaning is not unclear, because the speed of feeding chlorine gas may be adjusted by those skilled in the art depending on the monitoring results of the reaction.

The product prepared by the method of the present application has a high purity value. In some embodiments, trichloromethyl-substituted benzene with a purity of between about 70%-about 75%, between about 75%-about 80%, between about 80%-about 85%, between about 85%-about 90%, between about 90%-about 95%, or between about 95%-about 99.9% is directly obtained after the reaction, and preferably with a purity of between about 90.0%-about 90.5%, between about 90.0%-about 91.0%, between about 90.0%-about 91.5%, between about 90.0%-about 92.0%, between about 90.0%-about 92.5%, between about 90.0%-about 93.0%, between about 90.0%-about 93.5%, between about 90.0%-about 94.0%, between about 90.0%-about 94.5%, between about 90.0%-about 95.0%, between about 90.0%-about 95.5%, between about 90.0%-about 96.0%, between about 90.0%-about 96.5%, between about 90.0%-about 97.0%, between about 90.0%-about 97.5%, between about 90.0%-about 98.0%, between about 90.0%-about 98.5%, between about 90.0%-about 99.0%, between about 90.0%-about 99.1%, between about 90.0%-about 99.2%, between about 90.0%-about 99.3%, between about 90.0%-about 99.4%, between about 90.0%-about 99.5%, between about 90.0%-about 99.6%, between about 90.0%-about 99.7%, between about 90.0%-about 99.8%, or between about 90.0%-about 99.9% is directly obtained after the reaction.

If desired, trichloromethyl-substituted benzene obtained from the chlorination in the present invention may also be further purified via a conventional purification method such as recrystallization, rectification, or molecular distillation. The molecular distillation is preferred in the present invention.

The method of the present application may be run in a batch or continuous mode, preferably in a continuous mode.

Step 2 (chloroacylation reaction): further reacting the resulting trichloromethyl-substituted benzene in step 1 to prepare a chloroformyl-substituted benzene and to obtain a by-product hydrogen chloride.

The resulting chloroformyl-substituted benzene optionally is further purified or directly collected as a finished product; and the resulting by-product hydrogen chloride is recovered for use in step 3.

The chloroacylation reaction of the present invention comprises the following steps: fully melting the trichloromethyl-substituted benzene at an elevated temperature, adding water or the corresponding aromatic acid of formula $(X)_aC_6H_{6-a-b}(COOH)_b$ and a catalyst, and stirring thoroughly; wherein X is a chlorine, bromine or fluorine atom, a is an integer selected from 0, 1, 2, 3, 4 and 5, b is an integer selected from 1, 2, 3 and 4, and a+b≤6. The substituent on the parent nucleus of the aromatic acid and the substituent on the parent nucleus of the methyl aromatic hydrocarbon in step 1 may also be the same; and heating the reaction system to maintain the reaction, for example to 90-125° C., thereby obtaining a reaction mixture of the chloroacylation.

Preferably, trichloromethyl-substituted benzene and the corresponding aromatic acid are dosed in step i) at a stoichiometric molar ratio, for example bis-(trichloromethyl)-benzene and phthalic acid are dosed at a molar ratio of preferably 1:1.01-1.03. The catalyst in step i) is a Lewis acid, for example, aluminum trichloride, zinc chloride, ferric chloride, preferably ferric chloride; and particularly, when trichloromethyl-substituted benzene is reacted with water in step i), preferably, a small amount of the corresponding aromatic acid of formula $(X)_a C_6 H_{6-a-b}(COOH)_b$ is also present. The amount of the catalyst added in step i) is preferably 0.2%-0.3% of the mass of trichloromethyl-substituted benzene.

If desired, the resulting chloroformyl-substituted benzene from the chloroacylation may also be further purified via an optional purification method such as rectification, distillation, molecular distillation, or recrystallization. The rectification is preferred in the present invention.

The method of the present application may be run in a batch or continuous mode, preferably in a continuous mode.

Step 3 (catalytic oxidation of the by-product hydrogen chloride): subjecting the collected by-product hydrogen chloride in steps 1 and 2 to catalytic oxidation in the presence of a catalyst (the Deacon reaction) to prepare chlorine gas.

Optionally, the by-product hydrogen chloride gas is first pre-purified by a cryogenic or adsorption process to remove organic impurities before the catalytic oxidation. For example, hydrogen chloride gas may be purified by adsorption, and suitable adsorbent materials include, for example, activated carbon, aluminum oxide, titanium oxide, silica, ferric oxide, silica gel, zeolite, and a molecular sieve. In one aspect, step 3 of the present invention is directed to a method for preparing chlorine gas through catalytic oxidation of hydrogen chloride, comprising the steps of:

providing one or more reactors filled with a catalyst that are connected in series or in parallel;

providing a gas stream containing hydrogen chloride and a gas stream containing oxygen for oxidation of the gas stream containing hydrogen chloride to a first reactor of the one or more reactors, and providing a gas stream containing hydrogen chloride and/or a gas stream containing oxygen for oxidation of the gas stream containing hydrogen chloride to a downstream reactor of the one or more reactors, for the catalytic oxidation of hydrogen chloride;

directly returning a part of a product gas stream from a last reactor of the one or more reactors from the catalytic oxidation to any of the one or more reactors without separation thereof; and providing a remainder of the product gas stream from the last reactor of the one or more reactors for separation thereof.

The method of the present application may be run in a batch or continuous mode, preferably in a continuous mode.

In another aspect, step 3 of the present invention is directed to a method for preparing chlorine gas through catalytic oxidation of hydrogen chloride, comprising the steps of:

providing one or more reactors filled with a catalyst that are connected in series or in parallel;

providing a gas stream containing hydrogen chloride and a gas stream containing oxygen for oxidation of the gas stream containing hydrogen chloride to a first reactor of the one or more reactors, and providing a gas stream containing hydrogen chloride and/or a gas stream containing oxygen for oxidation of the gas stream containing hydrogen chloride to a downstream reactor of the one or more reactors, for the catalytic oxidation of hydrogen chloride;

before directly returning a part of a product gas stream from the last reactor of the one or more reactors to any of the one or more reactors without separation thereof, preferably to a feed inlet of any of the one or more reactors, mixing the part of the product gas stream from the last reactor of the one or more reactors with the gas stream containing hydrogen chloride and/or the gas stream containing oxygen for oxidation of the gas stream containing hydrogen chloride intended to enter any of the one or more reactors, which then is fed to said reactor for the catalytic oxidation; and providing a remainder of the product gas stream from the last reactor of the one or more reactors for separation thereof.

In one preferred embodiment of step 3 of the present invention, the gas stream containing hydrogen chloride and the gas stream containing oxygen for oxidation of a gas stream containing hydrogen chloride are provided to the first reactor of the one or more reactors, and the gas stream containing oxygen for oxidation of a gas stream containing hydrogen chloride is provided to a downstream reactor of the one or more reactors; and the gas streams containing oxygen for oxidation of a gas stream containing hydrogen chloride provided to the reactors are portions of a desired amount of a gas stream containing oxygen for oxidation of a gas stream containing hydrogen chloride that are distributed among the reactors in any ratio as desired, preferably equally distributed into corresponding parts according to the number of the reactors.

The preferred embodiment further preferably provides a method comprising the steps of:

providing one or more reactors filled with a catalyst that are connected in series or in parallel;

2a) providing a gas stream containing hydrogen chloride and a gas stream containing oxygen for oxidation of the gas stream containing hydrogen chloride to a first reactor of the one or more reactors, for the catalytic oxidation of hydrogen chloride;

2b) providing a product gas stream from the first reactor of the one or more reactors to a downstream reactor of the one or more reactors through a heat exchanger, providing a gas stream containing oxygen for oxidation of the gas stream containing hydrogen chloride to the downstream reactor of the one or more reactors, and successively providing a product gas stream from the previous reactor and a gas stream containing oxygen for oxidation of a gas stream containing hydrogen chloride to a remaining downstream reactor of the one or more reactors;

3) before returning a part of a product gas stream from the last reactor of the one or more reactors to any of the one or more reactors without separation thereof, preferably to a feed inlet of any of the one or more reactors, mixing the part of the product gas stream from the last reactor of the one or more reactors with the gas stream containing hydrogen chloride and/or the gas stream containing oxygen for oxidation of the gas stream containing hydrogen chloride intended to enter any of the one or more reactors, which then is fed to said reactor for the catalytic oxidation; and 4) providing a remainder of the product gas stream from the last reactor of the one or more reactors for separation thereof.

In another particular preferred embodiment of step 3 of the present invention, an oxygen content in the gas stream containing oxygen entering each of the reactors is greater than a theoretical oxygen consumption required for oxidation of the gas stream containing hydrogen chloride entering said reactor. The particularly preferred embodiment may be implemented by, for example, the method comprising: providing a gas stream containing oxygen for oxidation of a gas stream containing hydrogen chloride and a gas stream containing hydrogen chloride to a first reactor of the one or more reactors, and providing a gas stream containing hydrogen chloride to a downstream reactor of the one or more reactors; wherein the gas streams containing hydrogen chloride are portions of a gas stream containing hydrogen chloride to be oxidized that are distributed among the reactors in any ratio as desired, preferably equally distributed into corresponding parts according to the number of the reactors.

The particular preferred embodiment further preferably provides a method comprising the steps of:

providing one or more reactors filled with a catalyst that are connected in series or in parallel;

2a) providing a gas stream containing oxygen for oxidation of hydrogen chloride and a gas stream containing hydrogen chloride to a first reactor of the one or more reactors, for the catalytic oxidation of hydrogen chloride;

2b) providing a product gas stream from the first reactor of the one or more reactors to a downstream reactor of the one or more reactors through a heat exchanger, providing a gas stream containing hydrogen chloride to the downstream reactor of the one or more reactors, and successively providing a product gas stream from the previous reactor and a gas stream containing hydrogen chloride to a remaining downstream reactor of the one or more reactors;

3) before returning a part of a product gas stream from the last reactor of the one or more reactors to any of the one or more reactors without separation thereof, preferably to a feed inlet of any of the one or more reactors, mixing the part of the product gas stream from the last reactor of the one or more reactors with the gas stream containing hydrogen chloride and/or the gas stream containing oxygen for oxidation of the gas stream containing hydrogen chloride intended to enter any of the one or more reactors, which then is fed to said reactor for the catalytic oxidation; and 4) providing a remainder of the product gas stream from the last reactor of the one or more reactors for separation thereof.

Further, in returning a part of a product gas stream from the last reactor of the one or more reactors to any of the one or more reactors without separation thereof, the part of the product gas stream from the last reactor of the one or more reactors is preferably returned to each of the provided one or more reactors without separation thereof; and more preferably, before returning to a feed inlet of each of the one or more reactors, the part of the product gas stream from the last reactor of the one or more reactors is mixed with the gas stream containing hydrogen chloride and/or the gas stream containing oxygen for oxidation of the gas stream containing hydrogen chloride, which then is fed to said reactor for the catalytic oxidation. On the one hand, the method of the present invention can dilute the concentration of the feed reaction gas entering each of the one or more reactors to prevent the vigorous reaction at the inlet of said reactor and thus avoid the formation of too many hot spots; on the other hand, after the mixing is performed, the method of the present invention increases the feed temperature of the feed reaction gas, for which the preheating is not essentially required.

Further, in returning a part of a product gas stream from the last reactor of the one or more reactors to each of the provided one or more reactors without separation thereof, the returned product gas stream may be distributed among the one or more reactors in any ratio, for example, reasonably distributed depending on the operation conditions of the one or more reactors; wherein preferably, the returned product gas stream is equally distributed into corresponding parts according to the number of the one or more reactors, for respectively being returned to the one or more reactors. The one or more reactors in step 3 of the present application preferably are a adiabatic reactor. A heat exchanger may be connected between the reactors for reaction heat removal, namely, a heat exchanger is optionally present after each reactor. Preferably, the heat exchanger disposed after the last reactor is a gas heat exchanger, and the heat exchangers disposed after the rest of the reactors may be those well-known to a person skilled in the art, such as a tube bundle heat exchanger, plate heat exchanger, or gas heat exchanger.

It is preferred in the present application that, the remainder (or all after the reaction in step 3 is completed, and a person skilled in the art also can understand that the last portion of the product gas stream may not be returned) of the product gas stream (at a high temperature) from the catalytic oxidation in step 3 is passed through the gas heat exchanger before separation thereof, wherein the heat exchange is preferably performed in the gas heat exchanger using the gas stream containing hydrogen chloride and/or the gas stream containing oxygen for oxidation of the gas stream containing hydrogen chloride intended to enter the first reactor as a cooling medium; preferably, the gas stream containing hydrogen chloride and/or the gas stream containing oxygen for oxidation of the gas stream containing hydrogen chloride after being heat exchanged is mixed with a part of the returned product gas stream out of the third-stage reactor before being provided to the first reactor, and then is fed to the first reactor for the catalytic oxidation of hydrogen chloride. The temperature of the product gas stream is reduced after the heat exchange. The temperature of the gas stream containing hydrogen chloride and/or the gas stream containing oxygen for oxidation of the gas stream containing hydrogen chloride as the cooling medium is increased after the heat exchange, and then the gas stream containing hydrogen chloride and/or the gas stream containing oxygen for oxidation of the gas stream containing hydrogen chloride after being heat exchanged is provided to the first reactor for the catalytic oxidation of hydrogen chloride; preferably, the gas stream containing hydrogen chloride and/or the gas stream containing oxygen for oxidation of the gas stream containing hydrogen chloride after being heat exchanged is mixed with a part of the returned product gas stream out of the third-stage reactor before being provided to the first reactor, and then is fed to the first reactor for the catalytic oxidation of hydrogen chloride.

The step of providing a part or all of the product gas stream from step 3 for separation thereof in step 4 to obtain gas streams containing chlorine gas, containing oxygen, and/or containing hydrogen chloride in step 4 of the present invention means that a part or all of the product gas stream in step 3 is subjected to dehydration and removal of (some residues of) the gas stream containing hydrogen chloride and the gas stream containing oxygen, to obtain the gas stream containing chlorine.

It is preferred in the present application that (unreacted and residual) hydrogen chloride and/or oxygen gas separated in step 4 from the product gas stream may be provided again to the catalytic oxidation of step 3. The separated hydrogen chloride (or vaporized hydrochloric acid) and/or oxygen gas in step 4 may also be returned to the one or more reactors in step 3.

In all embodiments of the present invention, preferably, a volume ratio of the part of the product gas stream returned to the one or more reactors without separation thereof in step 3 (returned product gas stream) to the remainder of the product gas stream (remaining product gas stream) is 0.25:0.75-0.75:0.25, preferably 0.35:0.65-0.45:0.55. In all embodiments of the present invention, preferably, a feed volume ratio of the gas stream containing hydrogen chloride (calculated based on pure hydrogen chloride) to the gas stream containing oxygen gas (calculated based on pure oxygen) for oxidation of the gas stream containing hydrogen chloride is 1:2-5:1, preferably 1:1.2-3.5:1, more preferably 1:1-3:1.

In one preferred embodiment of step 3 of the present invention, a feed volume ratio of the gas stream containing hydrogen chloride (calculated based on pure hydrogen chloride) to the gas stream containing oxygen gas (calculated based on pure oxygen) for oxidation of the gas stream containing hydrogen chloride is 2:1-5:1.

In another particular preferred embodiment of step 3 of the present invention, a feed volume ratio of the gas stream containing hydrogen chloride (calculated based on pure hydrogen chloride) to the gas stream containing oxygen gas (calculated based on pure oxygen) for oxidation of the gas stream containing hydrogen chloride is 1:2-2:1, preferably 0.9:1.1-1.1:0.9.

In all embodiments of the present invention, preferably, the pressure within the one or more reactors is 0.1-1 MPa.

In all embodiments of the present invention, preferably, the feed gas temperature of the one or more reactors is 250-450° C., preferably 300-380° C.

The catalyst in step 3 of the present application is a conventional catalyst capable of reacting hydrogen chloride gas and oxygen gas via oxidation to generate chlorine gas and water. Suitable catalysts include a copper compound and/or a ruthenium compound, preferably a copper compound and/or a ruthenium compound loaded onto an alumina or titanium dioxide support, for example, alumina loaded with copper chloride or ruthenium chloride, preferably a ruthenium compound. The suitable catalysts according to the present application may also comprise other co-catalysts, for example, compounds of metals such as gold, palladium, platinum, osmium, iridium, nickel, or chromium, alkali metals, alkaline-earth metals, and rare earth metals. The suitable catalysts may have various shapes, for example, annular, cylindrical, spherical shapes, and it is preferred that the suitable catalysts have similar external dimensions.

The one or more reactors in step 3 of the present application are a conventional reactor, for example, a fixed bed or fluidized bed reactor, preferably a fixed bed reactor, which may be filled with a desired catalyst.

Reactors of any material that meets the requirements may be selected for the reactors according to the present application, and reactors made of pure nickel, nickel alloy, or quartz are preferred. If a plurality of reactors are selected, they may be connected in series or in parallel, preferably connected in series, such that the oxidation of hydrogen chloride may be performed in multiple stages. In the present application, preferably 2, 3, 4, 5, 6, 7, 8, 9, or 10, and more preferably 3 or 4 reactors are used. Advantageously, a person skilled in the art can understand that some raw material gases in the Deacon reaction are passed through the reactors in order, and then an additional gas stream containing hydrogen chloride and/or a gas stream containing oxygen for oxidation of hydrogen chloride is successively provided to the downstream reactors. In all embodiments of the present invention, preferably 2, 3, 4, 5, 6, 7, 8, 9, or 10, particularly preferably 3 or 4 adiabatic reactors connected in series are provided.

Particularly, reactors connected in series may also be combined with reactors connected in parallel. However, the method of the present invention particularly preferably has reactors that are only connected in series. If reactors connected in parallel are preferably used, then in particular, at most five, preferably three, particularly preferably at most two production lines (optionally comprising a reactor set consisting of reactors connected in series) are connected in parallel. Thus, the method of the present application may be operated with, for example, up to 60 reactors.

The method of the present application may be run in a batch or continuous mode, preferably in a continuous mode.

The "gas stream containing hydrogen chloride" according to the present application includes a fresh gas stream containing hydrogen chloride and a gas stream comprising the recovered hydrogen chloride by the method of the present invention or the recovered vaporized hydrochloric acid. The fresh gas stream containing hydrogen chloride may also be a gas stream containing hydrogen chloride as a by-product in related industries such as production of isocyanates, production of acid chlorides, or chlorination of aromatic compounds, preferably the gas stream containing hydrogen chloride as a by-product from steps 1 and 2 of the present invention. The gas streams containing hydrogen chloride as by-products may be gas streams containing hydrogen chloride as by-products that are preliminarily treated or gas streams containing hydrogen chloride as by-products directly from related industries that are not treated. The gas streams containing hydrogen chloride as by-products may contain little or no other impurity gases having no influence on the catalytic oxidation of hydrogen chloride and also resulting from the production processes in related industries, depending on the sources. The amounts of other impurity gases are determined by the nature of the production processes in related industries. A person skilled in the art can understand that the so-called waste hydrogen chloride generated in related industries may be a proper raw material for the present application.

The "unreacted gas stream containing hydrogen chloride" according to the present application refers to a gas stream containing hydrogen chloride that is not subjected to the catalytic oxidation through the reactors of the present application.

The "gas stream containing oxygen" according to the present application includes a fresh gas stream containing oxygen and a gas stream containing oxygen recovered by the method of the present invention. The fresh gas stream containing oxygen may be pure oxygen gas or other oxygen-containing gases (e.g. air).

The "product gas stream" according to the present application refers to a mixed gas comprising hydrogen chloride, oxygen gas, water vapor, and chlorine gas obtained from a reactor in which the catalytic oxidation is performed. Preferably, the returned product gas stream in the present invention is a mixed gas from the last reactor.

Step 4 (separation of the gas stream from step 3): separating the product gas stream from step 3 to obtain gas streams containing chlorine, containing oxygen, and/or containing hydrogen chloride.

The separation to obtain gas streams containing chlorine, containing oxygen, and/or containing hydrogen chloride in step 4 of the present invention comprises the steps of:

condensation: the product gas stream from step 3 is condensed; water in the product gas stream from step 3 along with a part of unreacted hydrogen chloride is condensed as an aqueous hydrochloric acid solution;

deep dehydration: the gas stream after being condensed in step a is subjected to deep dehydration, for example, through concentrated sulfuric acid, a molecular sieve, or by temperature swing adsorption, pressure swing adsorption, to remove residual moisture and reduce corrosiveness of the gas stream;

adsorption: the gas stream after being subjected to deep dehydration in step b is adsorbed by an adsorbent, to separate chlorine gas from oxygen gas.

On the one hand, the adsorption may use an adsorbent capable of adsorbing a large amount of oxygen gas and only a small amount of chlorine gas, such as a carbon molecular sieve and silica gels, to adsorb and remove oxygen gas; the treatment with the adsorbent generates a gas stream containing chlorine with chlorine gas as a main component, wherein a small amount of hydrogen chloride is optionally present. Oxygen gas adsorbed to the adsorbent after the treatment with the adsorbent is subjected to desorption, to obtain a separated gas stream containing oxygen; the adsorbent after the desorption may continue to be used in step c to adsorb and remove oxygen gas.

On the other hand, the adsorption may also use an adsorbent capable of adsorbing a large amount of chlorine gas and only a small amount of oxygen gas, such as fine-pored silica gel and activated carbon, to adsorb and remove chlorine gas, and the treatment with the adsorbent generates a gas stream containing oxygen with oxygen gas as a main component. Chlorine gas adsorbed to the adsorbent after the treatment with the adsorbent is subjected to desorption, to obtain a separated gas stream containing chlorine, wherein a small amount of hydrogen chloride is optionally present; the adsorbent after the desorption may continue to be used in step c to adsorb and remove chlorine gas.

And optionally, d. liquefaction: the gas stream containing chlorine obtained in step c is liquefied, to obtain a gas stream containing hydrogen chloride and a liquefied gas stream containing chlorine after separation thereof.

The condensation conditions in step a are: a temperature of −5-5° C. and a pressure of 0.05-10 MPa.

The specific operation process of temperature swing adsorption drying and pressure swing adsorption drying to remove residual moisture in step b and the specific operation process of separation of chlorine gas and oxygen gas by the pressure and temperature swing adsorption technology in step c can be found in patent application publication No. CN103752270A, which are briefly described below: the drying in step b is preferably performed using temperature swing adsorption drying or pressure swing adsorption drying, and a composite adsorbent layer with two adsorbents in combination is preferably used in the temperature swing adsorption drying wherein the one adsorbent is an alumina adsorbent placed in an upper portion of an adsorber and the other adsorbent is an adsorbent for dehydration placed in a lower portion of the adsorber, and a volume ratio of the upper alumina adsorbent to the lower adsorbent for deep dehydration is 20-80%:80%-20%. A composite adsorbent layer with two adsorbents in combination is preferably used in the pressure swing adsorption drying wherein the one adsorbent is an alumina adsorbent placed in an upper portion of an adsorber and the other adsorbent is an adsorbent for dehydration placed in a lower portion of the adsorber, and a volume ratio of the upper alumina adsorbent to the lower adsorbent for dehydration is 20-80%:80%-20%.

The temperature swing adsorption drying process in step b is that: the gas stream condensed in step a is passed through the composite adsorbent layer from bottom to top, and the drying is accomplished when the gas stream exits the temperature swing adsorption drying apparatus; in the temperature swing adsorption drying, the adsorption pressure is 0.30-0.80 MPa and the adsorption temperature is 20-50° C. The temperature swing adsorption drying process comprises alternative processes of adsorption and regeneration, wherein the alternative processes of adsorption and regeneration are performed by conventional arrangements (including depressurization, replacement, heating up, and cooling down). The regeneration operation includes desorption and dehydration processes. The desorption pressure of the regeneration operation is 0.01-0.005 MPa and the desorption temperature of the regeneration operation is 110-180° C.; the dehydration process of the regeneration operation uses a carrier gas at a temperature 50-180° C. (feed gas or nitrogen gas), and when the feed gas is used as a carrier gas for regeneration, the feed gas is dried through a pre-drying tower, heated through a steam heater, and fed to an adsorption drying tower to be heated for regeneration and dehydration, wherein the water-bearing carrier gas out of the adsorption tower is cooled, condensed, separated to remove water, and sent back to the feed gas system for recycle.

The pressure swing adsorption drying process in step b comprises alternative processes of adsorption and desorption, wherein the adsorption pressure is 0.40-0.80 MPa, the desorption pressure is 0.02-0.07 MPa, and the adsorption temperature is ambient temperature; the alternative processes of adsorption and desorption processes are performed by conventional arrangements (including pressure equalization, flushing replacement, and vacuum aspiration); the pressure swing adsorption drying process generally is a conventional four-tower process, wherein the flushing replacement uses a dried product gas stream, and tail gases of the flushing replacement and the vacuum aspiration are cooled and dehydrated and then sent to a product gas stream system for hydrogen chloride removal for recycle.

The adsorbent for the molecular sieve drying in step b is a zeolitic molecular sieve or silica gel.

The adsorption in step c preferably adopts the pressure and temperature swing adsorption technology including adsorption and desorption processes, wherein the adsorption pressure is 0.20-0.7 MPa, and the temperature in the adsorption stage is gradually decreased from 40-70° C. to 20-35° C.; the desorption pressure under reduced pressure is −0.07 MPa and the desorption temperature is 40-70° C.; in the adsorption, the gas stream as a feed gas at a temperature less than 40° C. is charged, the adsorption is started, and the temperature is reduced; before desorption for regeneration, hot chlorine gas at a temperature greater than 50° C. is charged to replace gas in the system, and the temperature is increased to facilitate desorption, and when the temperature reaches 40-70° C., the charging of hot chlorine gas is stopped and the vacuum desorption is started; after the desorption for regeneration is completed, oxygen is used to start the replacement before adsorption; both the tail gas replaced by hot chlorine gas and the tail gas replaced by oxygen gas are sent back to the feed gas system.

The "optionally step d" means that, when the ratio of hydrogen chloride to oxygen gas in the catalytic oxidation is appropriately controlled (for example, the ratio is 0.5:1-1:0.5 based on pure hydrogen chloride and pure oxygen), residual unreacted hydrogen chloride is substantially absorbed during the condensation by water generated in the reaction, and when the amount of hydrogen chloride in chlorine gas obtained in step c is comparatively small and does not affect the recycling of chlorine gas for the chlorination reaction, further liquefaction of chlorine gas to separate hydrogen chloride therefrom is not required; while when the ratio of hydrogen chloride to oxygen gas in the catalytic oxidation is at other values, some hydrogen chloride still remains after the treatments in steps a-c, and in this case, if necessary, the gas stream containing chlorine and hydrogen chloride may be liquefied in step d to separate out a gas stream containing hydrogen chloride.

The liquefaction conditions in step d are: a temperature of −20-20° C. and a pressure of 0.05-10 MPa.

Step 5 (recycling of the separated substances): introducing the gas stream containing chlorine separated in step 4 as a raw material into the chlorination reaction including step 1; and introducing the gas streams containing hydrogen chloride and/or containing oxygen separated in step 4 as a raw material into the catalytic oxidation reaction of the by-product hydrogen chloride including step 3.

The gas stream containing chlorine separated in step 4 may also be introduced into other independent chlorination reactions.

The purity of chlorine gas in the gas stream containing chlorine obtained by the catalytic oxidation in step 3 of the present invention is up to above 99.6% (vol %), which can meet the quality requirements of chlorine feed gas in the photochlorination reaction. The expression "closed circulation of chlorine resources (or chlorine element or chlorine atom)" in the present invention means that the by-product hydrogen chloride is suitably treated by the method of the present invention such that the chlorine element can be recycled in the method of the present invention.

The purity of the products, 1,3-bis-(trichloromethyl)-benzene, 1,4-bis-(trichloromethyl)-benzene, 1,3-bis-(chloroformyl)-benzene, 1,4-bis-(chloroformyl)-benzene, p-chloro-(trichloromethyl)benzene, and trichlorotoluene in the examples below is quantitatively determined by gas chromatography. The purify of the product 1,3,5-tris(trichloromethyl)benzene in the examples below is determined by liquid chromatography.

Example 1

As shown in the FIGURE, step 1, the chlorination reaction, is carried out as follows. In a continuous photochlorination apparatus consisting of 3 reaction columns connected in series, 1,3-dimethylbenzene is continuously added at a rate of 95 kg/h from the top of the first column, where the first column is controlled at a temperature of 80° C.-120° C., with a central peak wavelength of incident light of 460 nm and an average illuminance of 20000-39000 Lux, while chlorine gas is fed at a flow rate of 135 kg/h from the bottom for continuous chlorination reaction. The reaction solution in the first column overflows from the bottom into the second column, where the second column has central peak wavelength of incident light of 505 nm and an average illuminance of 40000-61000 Lux. The second column is controlled at a temperature of 135-145° C., and chlorine gas is fed at a flow rate of 128 kg/h into the second column. The reaction solution in the second column overflows from the bottom into the third column, where the third column has a central peak wavelength of incident light of 586 nm and an average illuminance of 60000-86000 Lux. The third column is controlled at a temperature of 170-180° C., and chlorine gas is fed at a flow rate of 148 kg/h into the third column. The total amount of chlorine gas fed in the reaction system consisting of the three columns is 411 kg/h. The resulting reaction mixture at the outlet of the third column is 1,3-bis-(trichloromethyl)-benzene, which is purified by single rectification to obtain purified 1,3-bis-(trichloromethyl)-benzene. The by-product hydrogen chloride gas generated in the photochlorination reaction is collected.

Step 2, chloroacylation reaction, is carried out as follows. The purified 1,3-bis-(trichloromethyl)-benzene obtained in step 1 is added to a batching kettle equipped with a temperature measuring device, a condensation reflux device, and a stirring device, where two or more batching kettles may be provided to achieve continuous feeding. 1,3-bis-(trichloromethyl)-benzene is heated to be completely melt. m-phthalic acid with a purity of 99.50% is added in a molar ratio of 1:1.01 of 1,3-bis-(trichloromethyl)-benzene:m-phthalic acid, and then ferric chloride catalyst is added in a weight ratio of 1:0.003 of 1,3-bis-(trichloromethyl)-benzene:ferric chloride. 1,3-bis-(chloroformyl)-benzene with a purity of 99.0% is added as a reaction solvent in a weight ratio of 1:1 of 1,3-bis-(trichloromethyl)-benzene:1,3-bis-(chloroformyl)-benzene. The raw materials for chloroacylation are heated and mixed in the batching kettle into a feedstock solution for chloroacylation, which is continuously added to two tandem chloroacylation reactors. The first-stage reactor is controlled at an inner temperature of 100° C., and the second-stage reactor has an inner temperature of 110° C. 1,3-bis-(chloroformyl)-benzene is obtained at the outlet of the second-stage reactor and is subjected to single rectification to obtain purified 1,3-bis-(chloroformyl)-benzene.

Step 3, catalytic oxidation of the by-product hydrogen chloride, is carried out as follows. The collected by-product hydrogen chloride in steps 1 and 2 is subjected to catalytic oxidation in the presence of a catalyst (the Deacon reaction) to prepare chlorine gas. The specific procedure is described below:

firstly, the by-product hydrogen chloride gas is purified by adsorption to remove organic impurities. The gas stream containing hydrogen chloride and the gas stream containing oxygen entering the first-stage reactor are mixed, preheated, and then fed to the first-stage reactor;

after passing through a heat exchanger, a gas stream from the first-stage reactor is mixed with other gas streams intended to enter the second-stage reactor (other gas streams refer to a returned product gas stream and a gas stream containing oxygen and/or a gas stream containing hydrogen chloride entering the reactor, the same hereinafter), and then enters the second-stage reactor; after passing through a heat exchanger, a gas stream from the second-stage reactor is mixed with other gas streams intended to enter the third-stage reactor, and then enters the third-stage reactor; and a product gas stream from the third-stage reactor is divided into two portions: one portion, returned product gas stream is equally distributed, returns to the inlets of the first-stage, second-stage, and third-stage reactors, mixes with a gas stream containing oxygen and/or a gas stream containing hydrogen chloride intended to enter each stage reactor, and then enters each stage reactor; and the other portion, remaining product gas stream is passed through a gas heat exchanger for heat exchange before separation thereof, where the gas stream containing hydrogen chloride and/or the gas stream containing oxygen for oxidation of the gas stream containing hydrogen chloride intended to enter the first reactor is used as a cooling medium.

Step 4, separation of the gas stream from step 3, is carried out as follows. The product gas stream from step 3 is separated to obtain gas streams containing chlorine, containing oxygen, or containing hydrogen chloride, which comprises the steps of:

condensation: the product gas stream from step 3 is condensed at a temperature of −5-5° C. and at a pressure of 0.05-10 MPa, water along with a part of unreacted hydrogen chloride is condensed as an aqueous hydrochloric acid solution;

deep dehydration: the gas stream after being condensed in step a is subjected to deep dehydration by using concentrated sulfuric acid;

adsorption: the gas stream after being subjected to deep dehydration in step b is passed though silica gel as an adsorbent to remove oxygen gas by adsorption, using the pressure and temperature swing adsorption technology, where the adsorption pressure is 0.5 MPa, and the temperature in the adsorption stage is gradually decreased from 60° C. to 25° C.; the desorption pressure under reduced pressure is −0.07 MPa and the desorption temperature is 50° C., and the desorption generates a separated gas stream containing oxygen. The remaining gas after adsorption is a gas stream containing chlorine with chlorine gas as a main component; and liquefaction: the gas stream containing chlorine obtained in step c is liquefied at a temperature of −20-20° C. and a pressure of 0.05-10 MPa, to obtain a gas stream containing hydrogen chloride and a liquefied gas stream containing chlorine after separation thereof.

Step 5, recycling of the separated substances, is carried out as follows. The gas stream containing chlorine separated in step 4 is introduced as a raw material into the chlorination reaction including step 1. The gas streams containing oxygen and containing hydrogen chloride separated in step 4 are introduced again as raw materials into the catalytic oxidation of hydrogen chloride including step 3. Specific process conditions are shown in Table 2. The reaction results are shown in Table 1.

Example 2

The specific operation process is described below.

Step 1, chlorination reaction

The operation process of the chlorination reaction is the same as step 1 in Example 1. The differences are that, 1,4-dimethylbenzene is used, the rate entering the first column is 100 kg/h, and the first column has a central peak wavelength of incident light of 460 nm and an average illuminance of 20000-39000 Lux; the second column has a central peak wavelength of incident light of 505 nm and an average illuminance of 40000-61000 Lux, and the second column is controlled at a temperature of 135-145° C.; and the third column has a central peak wavelength of incident light of 586 nm and an average illuminance of 60000-86000 Lux, and the third column is controlled at a temperature of 170-180° C. The resulting reaction mixture at the outlet of the third column is 1,4-bis-(trichloromethyl)-benzene, which is purified by single rectification to obtain purified 1,4-bis-(trichloromethyl)-benzene. The by-product hydrogen chloride gas generated in the photochlorination reaction is collected.

Step 2, chloroacylation reaction, is carried out as follows. The operation process of the chloroacylation reaction is the same as step 2 in Example 1. 1,4-bis-(chloroformyl)-benzene is obtained at the outlet of the second-stage reactor and is subjected to single rectification to obtain purified 1,4-bis-(chloroformyl)-benzene.

Step 3, catalytic oxidation of the by-product hydrogen chloride, is carried out as follows. The collected by-product hydrogen chloride in steps 1 and 2 is subjected to catalytic oxidation in the presence of a catalyst to prepare chlorine gas. The specific oxidation process comprises the steps of:

firstly, the by-product hydrogen chloride gas is purified by adsorption to remove organic impurities. The gas stream containing oxygen and the gas stream containing hydrogen chloride entering the first-stage reactor are mixed, preheated, and then fed to the first-stage reactor;

after passing through a heat exchanger, a gas stream from the first-stage reactor is mixed with other gas streams intended to enter the second-stage reactor, and then enters the second-stage reactor; after passing through a heat exchanger, a gas stream from the second-stage reactor is mixed with other gas streams intended to enter the third-stage reactor, and then enters the third-stage reactor; and a product gas stream from the third-stage reactor is divided into two portions: one portion, returned product gas stream is equally distributed, returns to the inlets of the first-stage, second-stage, and third-stage reactors, mixes with a gas stream containing oxygen and/or a gas stream containing hydrogen chloride intended to enter each stage reactor, and then enters each stage reactor; and the other portion, remaining product gas stream is passed through a gas heat exchanger for heat exchange before separation thereof, where the gas stream containing hydrogen chloride and/or the gas stream containing oxygen for oxidation of the gas stream containing hydrogen chloride intended to enter the first reactor is used as a cooling medium.

Step 4, separation of the gas stream from step 3

The product gas stream from step 3 is separated to obtain gas streams containing chlorine, containing oxygen, and containing hydrogen chloride, which comprises the steps of:

condensation: the product gas stream from step 3 is condensed at a temperature of −5-5° C. and at a pressure of 0.05-10 MPa, and water along with a part of unreacted hydrogen chloride is condensed as an aqueous hydrochloric acid solution;

deep dehydration: the gas stream after being condensed in step a is subjected to deep dehydration, wherein the drying is performed by the pressure swing adsorption technology using a composite adsorbent layer with two adsorbents in combination wherein the one adsorbent is an alumina adsorbent placed in an upper portion of an adsorber and the other adsorbent is a zeolitic molecular sieve adsorbent for deep dehydration placed in a lower portion of the adsorber, and a volume ratio of the upper alumina adsorbent to the lower adsorbent for deep dehydration is 40%:60%. In the pressure swing adsorption drying, the adsorption pressure is 0.40 MPa, the desorption pressure is 0.02 MPa, and the adsorption temperature is ambient temperature; and adsorption: the gas stream after being subjected to deep dehydration in step b is passed though a carbon molecular sieve as an adsorbent to remove oxygen gas by adsorption, using the pressure and temperature swing adsorption technology including adsorption and desorption processes, wherein the adsorption pressure is 0.20 MPa, and the temperature in the adsorption stage is gradually decreased from 40° C. to 20° C.; the desorption pressure under vacuum is −0.07 MPa and the desorption temperature is 40° C., and the desorption generated a separated gas stream containing oxygen. The remaining gas after adsorption is a gas stream containing chlorine with chlorine gas as a main component.

Step 5, recycling of the separated substances, is carried out as follows. The gas stream containing chlorine separated in step 4 is introduced as a raw material into the chlorination reaction including step 1. The gas stream containing oxygen separated in step 4 is introduced again as a raw material into the catalytic oxidation of hydrogen chloride including step 3. The reaction results are shown in Table 1, and specific process conditions are shown in Table 2.

Example 3

The operation is similar to the specific steps in Example 2, except the raw material methyl aromatic hydrocarbon is p-chlorotoluene, which is reacted with chlorine gas to obtain p-chloro-(trichloromethyl)benzene. The corresponding aromatic acid is p-chlorobenzoic acid.

Example 4

The operation is similar to the specific steps in Example 2, except the raw material methyl aromatic hydrocarbon is toluene, which is reacted with chlorine gas to obtain trichlorotoluene. The corresponding aromatic acid is benzoic acid.

Example 5

The operation is similar to the specific steps in Example 1, except the raw material methyl aromatic hydrocarbon is mesitylene, which is reacted with chlorine gas to obtain 1,3,5-tris(trichloromethyl)benzene. The corresponding aromatic acid is trimesic acid.

Example 6

Step 1, chlorination reaction, is carried out as follows. Into reaction columns, equipped with a temperature measuring device, a condensation reflux device, an illumination device of LED lamps, and a heating/cooling device, 100 kg of 1,3-dimethylbenzene is added and heated to 80° C. LED lamps are turned on for irradiation, with a central peak wavelength of incident light of 360 nm and an illuminance of 49000 Lux. Then, chlorine gas is fed to initiate the reaction while the feeding rate of chlorine gas is controlled so that the system temperature is no more than 120° C. The amount of chlorine gas consumed is 135.8 kg and the first reaction stage takes 4 h and 30 min. After the illuminance is adjusted to 60000 Lux and the system temperature is increased to 140° C., chlorine gas continued to be fed. The amount of chlorine gas consumed is 136 kg and the second reaction stage takes 3 h and 55 min. After the illuminance is maintained at 60000 Lux and the system temperature is increased to 160° C., 155.2 kg of chlorine gas continued to be fed. The third reaction stage takes 16 h and 35 min. The total amount of chlorine gas consumed in the reaction is 427 kg. The reaction mixture after the reaction is completed is a crude of 1,3-bis-(trichloromethyl)-benzene, which is purified by single rectification to obtain 255 kg of 1,3-bis-(trichloromethyl)-benzene with a purify of 99.42%. The gas generated in the chlorination reaction is collected to obtain 122 m³ of by-product hydrogen chloride.

Step 2, chloroacylation reaction, is carried out as follows. Into a reactor, equipped with a temperature measuring device, a condensation reflux device, and a stirring device, 255 kg of 1,3-bis-(trichloromethyl)-benzene with a purity of 99.42% obtained in step 1 is added and heated to be completely melt. 137.3 kg of m-phthalic acid with a purity of 99.50% is added in 1.01 times the mole number of 1,3-bis-(trichloromethyl)-benzene, and then 0.77 kg of ferric chloride catalyst is added in 0.30% of the weight of 1,3-bis-(trichloromethyl)-benzene. The temperature is raised to 110° C. for 60 min, at which the reaction is completed. The resulting product is subjected to rectification to obtain purified 1,3-bis-(chloroformyl)-benzene with a purity of 99.97%. The gas generated in the chloroacylation reaction is collected to obtain 34 m³ of by-product hydrogen chloride.

Step 3, catalytic oxidation of the by-product hydrogen chloride, is carried out as follows. The two by-product hydrogen chloride gases generated in the present example are continuously compressed into the catalytic oxidation system. The operation process is the same as step 3 in Example 2.

Step 4, separation of the gas stream from step 3, is carried out as follows. The product gas stream from step 3 is separated to obtain gas streams containing chlorine and containing oxygen, which comprises the steps of:

condensation: the product gas stream from step 3 is condensed at a temperature of −5-5° C. and at a pressure of 0.05-10 MPa, water along with a part of unreacted hydrogen chloride is condensed as an aqueous hydrochloric acid solution;

deep dehydration: the gas stream after being condensed in step a is subjected to deep dehydration, wherein the drying is performed by the temperature swing adsorption technology using a composite adsorbent layer with two adsorbents in combination wherein the one adsorbent is an alumina adsorbent placed in an upper portion of an adsorber and the other adsorbent is a zeolitic molecular sieve adsorbent for deep dehydration placed in a lower portion of the adsorber, and a volume ratio of the upper alumina adsorbent to the lower adsorbent for deep dehydration is 30%:70%. In the temperature swing adsorption drying, the adsorption pressure is 0.70 MPa and the adsorption temperature is 30° C.; the regeneration operation included desorption and dehydration processes. The desorption pressure of the regeneration operation is 0.009 MPa and the desorption temperature of the regeneration operation is 160° C.; the dehydration process of the regeneration operation uses a carrier gas at a temperature of 180° C.;

adsorption: the gas stream after being subjected to deep dehydration in step b is passed though a carbon molecular sieve as an adsorbent to remove oxygen gas by adsorption, using the pressure and temperature swing adsorption technology including adsorption and desorption processes, wherein the adsorption pressure is 0.5 MPa, and the temperature in the adsorption stage is gradually decreased from 60° C. to 25° C.; the desorption pressure under reduced pressure is −0.07 MPa and the desorption temperature is 50° C., and the desorption generates a separated gas stream containing oxygen. The remaining gas after adsorption is a gas stream containing chlorine with chlorine gas as a main component; and liquefaction: the gas stream containing chlorine obtained in step c is liquefied at a temperature of −20-20° C. and a pressure of 0.05-10 MPa, to obtain a gas stream containing hydrogen chloride and a liquefied gas stream containing chlorine after separation thereof.

The amount of chlorine gas obtained after separation thereof in step 4 is determined to be 195 Kg, with a purity of 99.97(v. %), and the amount of recovered hydrogen chloride obtained after separation thereof is 18 m³; and the amount of recovered oxygen gas obtained after separation thereof is 30 m³.

Step 5, recycling of the separated substances, is carried out as follows. The gas stream containing chlorine separated in step 4 is introduced as a raw material into the chlorination reaction including step 1, and the resulting crude is purified by single rectification to obtain 1,3-bis-(trichloromethyl)-benzene with a purity of 99.4%. Further, the purified 1,3-bis-(trichloromethyl)-benzene is introduced into the chloroacylation reaction including step 2, to obtain 1,3-bis-(chloroformyl)-benzene with a purity of 99.96%. The reaction results are shown in Table 1.

Table 1 below shows input and output amounts of main materials in Examples 1-5; and Table 2 shows operation conditions for the oxidation unit in step 2 of the respective Examples.

The trichloromethyl-substituted benzene purity (%) in the table refers to the purity of a sample obtained by introducing a separated, recovered gas stream containing chlorine into the chlorination reaction which includes step 1, thereby obtaining a trichloromethyl-substituted benzene crude product which is then purified via a single rectification to obtain the sample; the chloroformyl-substituted benzene purity (%) in the table refers to the purity of a sample obtained by introducing the resulting trichloromethyl-substituted benzene mentioned above into the chloroacylation reaction which includes step 2, thereby obtaining a chloroformyl-substituted benzene crude product which is then purified via a simple rectification to obtain the sample.

TABLE 1

Input and output amounts of main materials in the clean process

| | Chlorination reaction | | | | | | | Catalytic oxidation | Separation of product gas stream | | | |
|---|---|---|---|---|---|---|---|---|---|---|---|---|
| | Methyl aromatic hydrocarbon | | $Cl_2$ | HCl | TCM-SB | TCM-SB | | | $O_2$ | HCl | $O_2$ | $Cl_2$ gas recovered |
| Ex | Species | Amount (Kg/h) | gas (Kg/h) | HCl ($m^3$/h) | Purity (%) | yield (Kg/h) | yield ($m^3$/h) | TCM-SB Purity (%) | used ($m^3$/h) | recovered ($m^3$/h) | recovered ($m^3$/h) | Yield | Purity (v.%) |
| 1 | 1,3-dimethylbenzene | 95 | 411 | 117 | 99.12 | 252 | 33 | 99.97 | 49.9 | 17 | 18 | 186 Kg/h | 99.98 |
| 2 | 1,4-dimethylbenzene | 100 | 435 | 122 | 99.23 | 245 | 32 | 99.96 | 309.3 | / | 267 | 73 $m^3$/h | 99.97 |
| 3 | p-chlorotoluene | 85.5 | 156 | 43 | 99.86 | 143 | 12 | 99.95 | 55.2 | / | 40 | 25 $m^3$/h | 99.97 |
| 4 | toluene | 125 | 312 | 89 | 99.9 | 250 | 26 | 99.98 | 141 | / | 111 | 54 $m^3$/h | 99.96 |
| 5 | Mesitylene | 92.6 | 530 | 153 | 99.43 | 312 | 47 | 99.96 | 40 | 46 | 13 | 156 Kg/h | 99.98 |

(TCM-SB = trichloromethyl-substituted benzene)

Notes:
Chlorine gas consumed in the chlorination step may comprise recovered gas streams containing chlorine separated in steps 4 and 5; Hydrogen chloride used in step 3 of the examples of the present invention is the total amount of hydrogen chloride generated by the chlorination in step 1 and the chloroacylation in step 2; those skilled in the art can understand that, a gas stream containing hydrogen chloride other than that generated in steps 1 and 2 of the present invention may also be introduced in actual production process. Recovered hydrogen chloride and recovered oxygen gas from the catalytic oxidation of step 3 may be recycled through step 5 to participate in the catalytic oxidation of hydrogen chloride.

TABLE 2

Catalytic oxidation process of step 3

| | Example | | | | | |
|---|---|---|---|---|---|---|
| | 1 | 2 | 3 | 4 | 5 | 6 |
| Volume ratio returned:remaining product gas stream | 0.5:0.5 | 0.3:0.7 | 0.5:0.5 | 0.3:0.7 | 0.3:0.7 | 0.4:0.6 |
| Feeding HCl-containing gas stream | All enter 1st reactor | Separate reactors at volume ratio 0.5:1:1.5 | Separate reactors at volume ratio 1:1:1 | Separate reactors at volume ratio 0.5:1:1.5 | All enter 1st reactor | Separate reactors at volume ratio 1:1:1 |
| Feeding $O_2$-containing gas stream | Separate reactors at volume ratio 1:1:1 | All enter 1st reactor | All enter 1st reactor | All enter 1st reactor | Separate reactors at volume ratio 1:1:1 | All enter 1st reactor |
| Feed volume ratio HCl:$O_2$ | 3:1 | 1:2 | 1:1 | 0.9:1.1 | 5:1 | 2.5:1 |
| HCl-containing gas stream (based on pure HCl) ($m^3$/h) | 149.7 | 154.6 | 55.2 | 115.4 | 200 | 157.1 |
| $O_2$-containing gas stream (based on pure $O_2$) ($m^3$/h) | 49.9 | 309.3 | 55.2 | 141 | 40 | 62.8 |
| Feed temp. of 1st reactor (° C.) | 310 | 325 | 360 | 313 | 313 | 325 |
| Catalyst | Ru—Cu composite catalyst 1 | Ru—Cu composite catalyst 2 | Ru—Cu composite catalyst 1 | Ru—Cu composite catalyst 2 | Ru—Cu composite catalyst 2 | Ru—Cu composite catalyst 2 |

We claim:

1. A process for preparing a chloroformyl-substituted benzene, comprising
   (1) reacting a methyl aromatic hydrocarbon of formula $(X)_aC_6H_{6-a-b}(CH_3)_b$ or a pendant alkyl chloride thereof with chlorine gas under illumination conditions to prepare a trichloromethyl-substituted benzene and obtain hydrogen chloride as a byproduct, wherein X is a chlorine, bromine, or fluorine atom, a is an integer of 0, 1, 2, 3, 4, or 5, b is an integer of 1, 2, 3, or 4, and a+b≤6, and the pendant alkyl chloride is a compound where hydrogen atoms of the pendant alkyl group in the methyl aromatic compound are not completely substituted by chlorine atoms;
   (2) reacting the trichloromethyl-substituted benzene with water or a corresponding aromatic acid of formula $(X)_aC_6H_{6-a-b}(COOH)_b$ in presence of a catalyst to prepare the chloroformyl-substituted benzene and to obtain hydrogen chloride as a byproduct, wherein the corresponding aromatic acid $(X)_aC_6H_{6-a-b}(COOH)_b$ has the same substituent $(X)_a$ that is located at the same substitution position as the substituent $(X)_a$ of the methyl aromatic hydrocarbon $(X)_aC_6H_{6-a-b}(CH_3)_b$ or the pendant alkyl chloride thereof;
   (3) subjecting a gas stream containing the hydrogen chloride as the byproducts from steps (1) and (2) to catalytic oxidation in one or more reactors to form a product gas stream, wherein the catalytic oxidation is conducted by
      providing a first reactor and one or more downstream reactors, each of the reactors being filled with a catalyst and connected in series or in parallel,
      providing a gas stream containing hydrogen chloride and a gas stream containing oxygen to the first reactor and providing a gas stream containing hydrogen chloride, a gas stream containing oxygen, or both, to the downstream reactor for the catalytic oxidation of hydrogen chloride to obtain a product gas stream;
      directly returning a part of the product gas stream from the last reactor to any of the reactors without separation of products; and
      providing a remainder of the product gas stream from the last reactor for separation of a product;
   (4) separating the remainder of the product gas stream to obtain a gas stream containing chlorine, a gas stream containing oxygen, and optionally, a gas stream containing hydrogen chloride; and
   (5) introducing the gas stream containing chlorine as raw material into chlorination reaction in step (1).

2. The process according to claim 1, further comprising introducing the gas stream containing hydrogen chloride, the gas stream containing oxygen, or both, as raw material into catalytic oxidation in step (3).

3. The process according to claim 1, further comprising mixing the part of the product gas stream from the last reactor with the gas stream containing hydrogen chloride, the gas stream containing oxygen, or both, to obtain a mixed gas before returning the part of the product gas stream to any of the reactors, and feeding the mixed gas to any of the reactor via a feed inlet for the catalytic oxidation.

4. The process according to claim 1, further comprising returning the part of the product gas stream from the last reactor to each of the reactors without separation of products.

5. The process according to claim 4, wherein the part of the product gas stream from the last reactor is returned at an equally distributed ratio to each of the reactors.

6. The process according to claim 1, wherein the gas stream containing hydrogen chloride and the gas stream containing oxygen are provided to the first reactor, and the gas stream containing oxygen is provided to the one or more downstream reactors.

7. The process according to claim 6, wherein the gas streams containing oxygen is provided at an equally distributed ratio to each of the one or more downstream reactors.

8. The process according to claim 1, wherein the gas stream containing oxygen and the gas stream containing hydrogen chloride are provided to the first reactor, and the gas stream containing hydrogen chloride is provided to the one or more downstream reactors; and
   an oxygen content in the gas stream containing oxygen entering each of the one or more downstream reactors is greater than a theoretical oxygen consumption amount required for oxidation of the gas stream containing hydrogen chloride entering the same reactor.

9. The process according to claim 8, wherein the gas streams containing hydrogen chloride are portions of a gas stream containing hydrogen chloride to be oxidized that are equally distributed into each of the one or more downstream reactors.

10. The process according to claim 1, further comprising
    providing a product gas stream from the first reactor to one of the one or more downstream reactors through a heat exchanger,
    providing a gas stream containing oxygen to the downstream reactor to obtain a subsequent product gas stream,
    successively providing the subsequent product gas stream from the previous reactor and a gas stream containing oxygen to the remaining reactor of the one or more downstream reactors;
    mixing a part of the product gas stream from the last reactor with the gas stream containing hydrogen chloride, the gas stream containing oxygen, or both, before returning the part of the product gas stream from the last reactor to any of the reactors without separation of products to obtain a mixed gas, and
    feeding the mixed gas to the reactors for the catalytic oxidation.

11. The process according to claim 1, further comprising
    providing a product gas stream from the first reactor to one of the one or more downstream reactors through a heat exchanger,
    providing a gas stream containing hydrogen chloride to the downstream reactor for reaction to obtain a subsequent product gas stream,
    successively providing the subsequent product gas stream from the previous reactor and a gas stream containing hydrogen chloride to the remaining of the one or more downstream reactors,
    mixing a part of the product gas stream from the last reactor of the one or more downstream reactors with the gas stream containing hydrogen chloride, the gas stream containing oxygen for oxidation, or both, to form a mixed gas, before returning the part of the product gas stream from the last reactor to any of the one or more reactors without separation of products, and
    feeding the mixed gas to the reactor for the catalytic oxidation.

12. The process according to claim 1, wherein each of the one or more reactors in step (3) has a heat exchanger disposed thereafter for removing reaction heat, and the heat exchanger is a tube bundle heat exchanger, a plate heat exchanger, or a gas heat exchanger.

13. The process according to claim 12, wherein the remainder of the product gas stream from the last reactor passes through the heat exchanger before separation of products,
- heat exchange is performed in the heat exchanger using the gas stream containing hydrogen chloride, the gas stream containing oxygen, or both, for entering the first reactor as a cooling medium, and
- the gas stream containing hydrogen chloride, the gas stream containing oxygen, or both, after being heat exchanged, is mixed with a part of a returned product gas stream out of the last reactor of the one or more reactors before being provided to the first reactor, and then is fed to the first reactor for the catalytic oxidation of hydrogen chloride.

14. The process according to claim 1, wherein volume ratio of the part of the product gas stream from the last reactor to the one or more reactors without separation of products to the remainder of the product gas stream from the last reactor is 0.25:0.75 to 0.75:0.25.

15. The process according to claim 1, wherein feed volume ratio of the gas stream containing hydrogen chloride calculated based on pure hydrogen chloride to the gas stream containing oxygen calculated based on pure oxygen is 1:2 to 5:1.

16. The process according to claim 1, wherein feed volume ratio of the gas stream containing hydrogen chloride calculated based on pure hydrogen chloride to the gas stream containing oxygen calculated based on pure oxygen is 2:1 to 5:1.

17. The process according to claim 1, wherein a feed volume ratio of the gas stream containing hydrogen chloride calculated based on pure hydrogen chloride to the gas stream containing oxygen calculated based on pure oxygen is 1:2 to 2:1.

18. The process according to claim 1, wherein the product gas stream from step (3) is separated in step (4) by
- condensing the product gas stream from step (3), wherein water generated by the reaction in step (3) and part of unreacted hydrogen chloride are condensed as an aqueous hydrochloric acid solution;
- subjecting the product gas stream after being condensed to deep dehydration, wherein deep hydration is conducted through treatment with concentrated sulfuric acid, molecular sieve, temperature swing adsorption, or pressure swing adsorption, to remove residual moisture;
- adsorbing the gas stream after being subjected to deep dehydration by an adsorbent to separate chlorine gas from oxygen gas; and optionally,
- liquefying the gas stream containing chlorine obtained after adsorption to obtain a gas stream containing hydrogen chloride and a liquefied gas stream containing chlorine.

19. The process according to claim 1, wherein step (1) is carried out by
- reacting the methyl aromatic hydrocarbon with chlorine gas under illumination to obtain trichloromethyl-substituted benzene,
- the illumination uses a light source having a wavelength of about 350 nm to 700 nm and a light amplitude of no more than about 200 nm, and
- the chlorine gas is initially fed at a temperature of about 0° C. to 85° C. and an illuminance of about 2000 Lux to about 55000 Lux for a first reaction stage, and the first reaction stage is conducted at a reaction temperature of no more than about 120° C. at the illuminance, and
- the remaining amount of chlorine gas is continuously fed at a reaction temperature higher than the reaction temperature at the first reaction stage.

20. The process according to claim 19, wherein the light source is an LED lamp.

21. The process according to claim 1, further comprising
- prepare the chloroformyl-substituted benzene in step (2) by fully melting the trichloromethyl-substituted benzene at an elevated temperature, adding the water or the corresponding aromatic acid and a catalyst, and stirring thoroughly; and
- heating and maintaining reaction system at an elevated temperature while conducting the reaction.

* * * * *